United States Patent [19]

Schneiderman

[11] 4,301,801
[45] Nov. 24, 1981

[54] ELECTROSURGE FAILSAFE SYSTEM

[75] Inventor: Max Schneiderman, Clifton, N.J.

[73] Assignee: IPCO Hospital Supply Corporation (Whaledent International Division), New York, N.Y.

[21] Appl. No.: 12,831

[22] Filed: Feb. 16, 1979

[51] Int. Cl.³ .................................... A61B 17/36
[52] U.S. Cl. .......................... 128/303.14; 128/303.17; 128/908; 307/100; 361/52; 361/91
[58] Field of Search ............... 128/303.13, 303.14, 128/303.17, 908; 307/100, 326; 361/21, 52, 91; 328/7, 8, 259; 323/9, 81

[56] References Cited

U.S. PATENT DOCUMENTS

| | | | |
|---|---|---|---|
| 2,976,462 | 3/1961 | Miller | 328/7 X |
| 3,359,434 | 12/1967 | Galluzzi | 328/8 X |
| 3,493,815 | 2/1970 | Hurtle | 361/91 X |
| 3,683,923 | 8/1972 | Anderson | 128/303.14 |
| 3,730,188 | 5/1973 | Ellman | 128/303.17 |
| 3,875,945 | 4/1975 | Friedman | 128/303.14 |
| 3,931,546 | 1/1976 | Jakobs et al. | 361/52 X |
| 4,094,320 | 6/1978 | Newton et al. | 128/303.14 |
| 4,122,854 | 10/1978 | Blackett | 128/303.13 |

FOREIGN PATENT DOCUMENTS

| | | | |
|---|---|---|---|
| 855459 | 11/1960 | United Kingdom | 128/303.17 |
| 897961 | 6/1962 | United Kingdom | 128/303.14 |

Primary Examiner—Lee S. Cohen
Attorney, Agent, or Firm—Friedman, Goodman & Teitelbaum

[57] ABSTRACT

An electrosurge generator, which is energized by a power supply to produce an output voltage of a desired level, includes a failsafe system at its output to prevent any excessive high DC voltage output which may result from a failure in the electrosurge generator. The failsafe system has a detection element coupled to the output of the electrosurge generator which detects any output above a predetermined threshold. A switching circuit is activated by the detection element. The switching circuit is connected across the power supply, and when activated, removes the power supplied from the power supply to the electrosurge generator.

10 Claims, 3 Drawing Figures

ELECTROSURGE FAILSAFE SYSTEM

BACKGROUND OF THE INVENTION

This invention relates to electrosurge generators having protective circuits at their output, and more specifically to an electrosurgical unit having a failsafe circuit at its output.

Electrosurge generators generally refer to systems which provide a high voltage output for application to various uses. The electrosurge generator is energized by a power supply in order to produce its high voltage output. Typical of such systems is an electrosurgical unit which includes an RF generator whose output is applied to a probe or blade, and is used during the course of surgical procedures.

In connection with electrosurgical units, it has been found that when the RF output is unmodulated, the output can be used for tissue cutting. On the other hand, by utilizing a pulse modulated RF voltage signal, coagulation of blood vessels can be achieved.

With such electrosurgical units, there is typically provided an oscillator having an output circuit which selectively produces the modulated or unmodulated output. The output circuit typically includes an output tank coil to which is connected an output device such as a probe, forceps or a blade.

During normal operation, the output voltage, whether modulated or unmodulated, is controlled by means of an intensity control knob to produce the desired voltage level. However, should there be a component failure or other failure within the electrosurgical unit, there exists the possibility of an extremely high voltage being applied at the output. Specifically, there is a potentially lethal internal DC power supply voltage which because of failures of certain components therein could appear at the patient contacting electrotip, and thus could cause severe traumatic effect, patient tissue damage, and in some instances, tragic results.

While there may exist in the prior art various components placed at the output of such electrosurgical units for protecting the patient, most of these components were designed to block the internal DC power supply voltage of the electrosurgical unit from the probe or other such device. As long as the particular protective components are operative, some protection could be afforded to the patient. However, should the components themselves fail, then the high internal voltage would be applied to the patient and the protective circuit itself is ineffective.

SUMMARY OF THE INVENTION

It is therefore an object of the present invention to provide an electrosurge system with an improved failsafe system.

A further object of the present invention is to provide an electrosurge generator including a failsafe circuit at its output which prevents excessive high voltage resulting from failure of the electrosurge system.

Yet another object of the present invention is to provide an electrosurge generator unit having a failsafe circuit which serves to disable power supplied to the electrosurge generator itself.

A further object of the present invention is to provide an electrosurgical unit having a failsafe circuit at its output which serves to disable power to the electrosurgical unit upon detection of a system failure.

Briefly, in accordance with the present invention, a failsafe system which is applied at the output of the electrosurge generator serves to detect a high voltage output resulting from a system or component failure, and in response thereto disables the power directly being sent to the electrosurge generator.

More specifically, the present invention provides a failsafe circuit for an electrosurge generator. The electrosurge generator is energized by a power supply and produces an output voltage of a desired level. The protective circuit prevents an excessive high DC voltage output from the electrosurge generator which may result from a failure in the generator. The failsafe circuit comprises a detection circuit coupled to the output of the electrosurge generator which detects an output above a predetermined threshold value. A switching circuit is activated by the detection circuit. The switching circuit is connected across the power supply and upon activation removes the power supplied to the electrosurge generator.

In a specific embodiment of the present invention, the electrosurge generator is an electrosurgical unit providing both an unmodulated and modulated RF output voltage. The RF voltage is produced by an oscillator having a tank output circuit. Connected at the output of the tank circuit is the gate of an SCR whose main current carrying terminals are connected in parallel between the power supply and a ground terminal. Upon detecting a high output, the SCR is triggered to thereby short circuit the power supply, thereby causing a fuse in series with the power supply to break. This interrupts the entire power sent to the system.

BRIEF DESCRIPTION OF THE DRAWINGS

With the above and additional objects and advantages in view, as will hereinafter appear, this invention comprises the devices, combinations, and arrangements of parts hereinafter described by way of example and illustrated in the accompanying drawings of a preferred embodiment in which.

DETAILED DESCRIPTION OF THE PREFERRED EMBODIMENT

Figure 1:
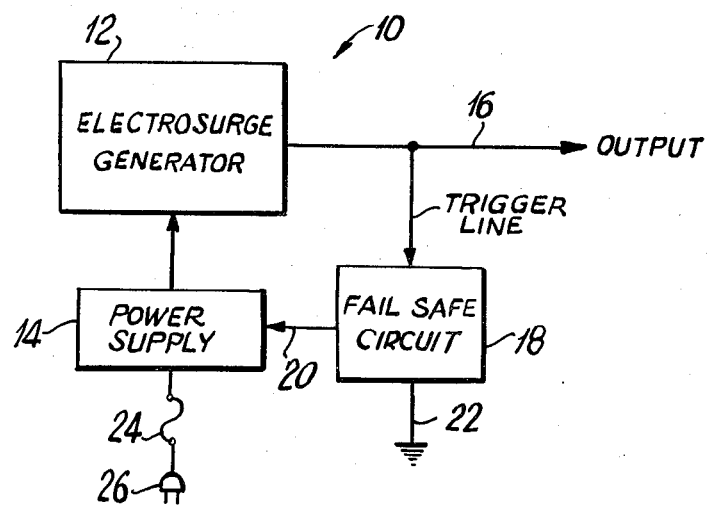
FIG. 1 is a block diagram of an electrosurge system of the present invention.

Referring now to FIG. 1, there is generally shown the operation of the failsafe system of the present invention. The system is generally referred to as the electrosurge system 10 which includes an electrosurge generator 12 energized by a power supply 14. The electrosurge generator typically produces an output along line 16. A failsafe circuit 18 monitors the output of the electrosurge generator. The failsafe circuit receives an input along the trigger line from the output line 16. The failsafe circuit is connected to the power supply along line 20, and has another line 22 coupled to ground.

Upon detecting an output on line 16 above a predetermined threshold value, the failsafe circuit 18 operates to remove the power supply from the electrosurge generator 12. This can typically be achieved by short circuiting the power supply 14 to ground. As a result, the short circuited power supply no longer sends its power to energize the electrosurge generator.

In order to further ensure that the power supply will not send any power to the electrosurge generator, the power supply can include a fuse 24 connected in series between the output plug 26 and the power supply 14. The plug 26 is inserted into a conventional power source (not shown) to energize the power supply. When the power supply becomes short circuited by means of the failsafe circuit, the fuse 24 will be broken to thereby completely interrupt power to the entire system. As a result, the entire electrosurge system 10 becomes completely inoperative. This completely prevents any damage which may result from the high output level on line 16.

It should be appreciated that other prior art protective devices also may have been connected to the output of the electrosurge generator. These other prior art devices would serve to disconnect the output of the electrosurge generator from its further use. However, the electrosurge generator itself continues to operate and still receives power from the power supply. As a result, the high voltage is still available at the output. Although the high voltage output is not applied for use, its availability still provides a potential danger. For example, if one of the components would fail, there exists the possibility that the output of the electrosurge generator would still be applied to the utilization circuit. Furthermore, since this high voltage is still available in the generator, someone might accidentally touch part of the system and would be harmed by this voltage. With the present failsafe circuit, upon detection of the high DC voltage output above a predetermined threshold, the entire system is disconnected whereby no power is sent to the electrosurge generator and, in an embodiment of the present invention, the power supply itself is disconnected from its source.

Figure 2:
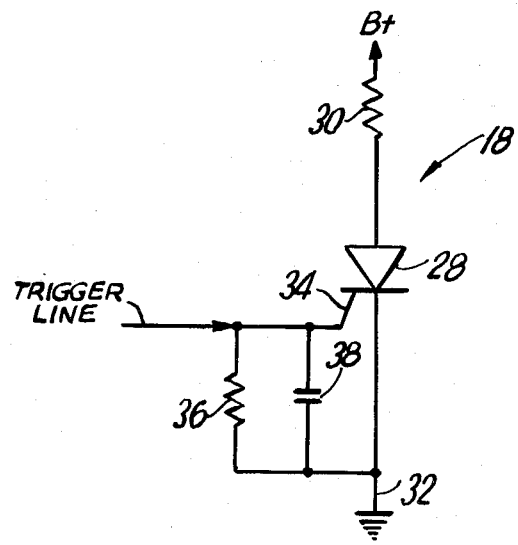
FIG. 2 is a schematic showing of the failsafe circuit of the present invention.

Referring now to FIG. 2, there is shown one embodiment of the failsafe circuit 18. Specifically, the failsafe circuit 18 includes a thyristor device, herein shown as an SCR 28 whose anode is connected by means of the resistor 30 to the positive terminal of the power supply, designated as B+. The cathode is connected to ground 32. The trigger or gate terminal 34 is connected to the output of the electrosurge generator to sense DC voltage in the output along the trigger line. Connected in parallel between the gate and the ground terminals is a resistor 36 in parallel with a capacitor 38.

The operation of the circuit shown in FIG. 2 is as follows. The failsafe circuit monitors the output from the electrosurge generator. Under normal operation, the SCR is inoperative and the electrosurge generator can apply its output DC voltage directly to a utilization device. Upon detection of a dangerously high DC output, the gate 34 of the SCR will be triggered by the trigger line. This will turn on the SCR to provide a very low impedance path. The SCR being interconnected directly across the power supply, will short circuit the power supply. The power supply will therefore be grounded through the SCR and prevent its output from going towards the electrosurge generator. Accordingly, the power supply is short circuited thereby preventing any current from passing to the electrosurge generator, and accordingly the current at the output of the electrosurge generator is not diverted through the switching circuit. If a fuse is included in the supply line to the power supply, the fuse will break and thereby interrupt any power directly to the power supply to thereby completely make the entire system inoperative.

Resistor 30 is included and is placed at a value high enough to limit the short circuit current in the SCR to a safe value. At the same time, its value should be low enough to cause a severe overload across the power supply when the SCR is turned on. Resistor 36 provides a low impedance path to ground for any device leakage current which might otherwise cause premature triggering of the device. The capacitor 38 filters out any RF or switching transients which might cause premature triggering of the SCR.

The SCR itself is chosen from a wide selection of presently available types and manufacturers. The important parameters in choosing an appropriate SCR device are the repetitive peak off stage voltage, the DC gate trigger current, and the critical rate of rise of the off stage voltage. However, selection of an appropriate SCR device is well within the state of the art.

Figure 3:
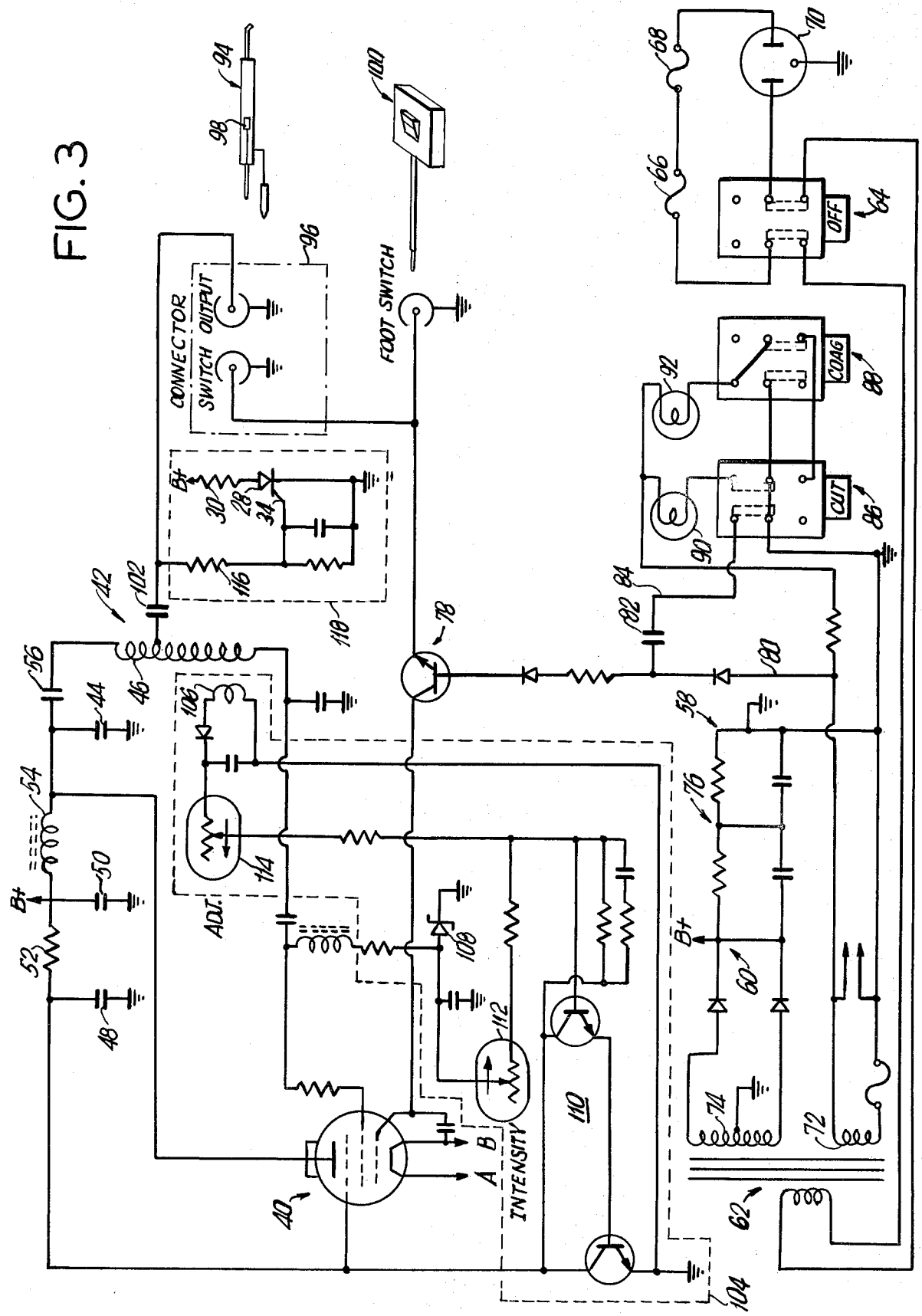
FIG. 3 is a detailed circuit diagram showing a particular electrosurgical unit having the failsafe system included in its output.

In order to show the use of the present failsafe system, reference is had to FIG. 3 which shows a currently available electrosurgical unit. Such electrosurgical unit is described in my U.S. Pat. No. 4,092,986, assigned to the assignee of the present invention. All of the material of that U.S. patent is incorporated herein by reference.

Although details of the circuit are described in my aforementioned patent, the circuit will be briefly described in order to better understand the operation of the failsafe system in conjunction with the main electrosurgical unit. The electrosurgical unit includes an oscillator 40 of the well known Clapp oscillator type having a vacuum tube provided with a plate connected to a tank circuit shown generally at 42 which includes a tuning capacitor 44 and a tank coil 46. The output is tapped off from the tank coil 46.

Included in the plate and screen grid circuits are the by-pass capacitors 48, 50 and the screen dropping resistor 52. An RF choke 54 isolates the tank coil from the power source. A blocking capacitor 56 is also included in the tank circuit.

The plate of the oscillator is energized by means of the voltage from a power supply, shown generally at the bottom of the circuit at 58. The power supply includes a full wave rectifier 60 which receives power across a transformer 62. The primary of the transformer passes through an on-off switch 64. Power to the system is provided in series with the fuses 66 and 68 from a plug 70 connected to a source of power. The secondary 72 is utilized to provide the output at points A, B to the filament of the oscillator 40. The other secondary 74 provides the B+ power supply across a filter network 76.

The control grid of the oscillator is coupled to appropriate resistors, RF chokes, blocking capacitors, etc. The cathode of the oscillator is connected to a switching circuit including the switching transistor shown generally at 78. The transistor is utilized to change the output of the oscillator between a modulated and unmodulated output. The base of the transistor has one side connected to line 80 on the one hand, and through capacitor 82 to the line 84, on the other hand. The two switches 86, 88 are respectively utilized to provide an unmodulated output for a cutting procedure, and a modulated output for a coagulation procedure. The two switches are interconnected to prevent simultaneous operation thereof. The indicator bulbs 90 and 92 are available to provide the user with an indication of which output is being provided.

The output is available through a probe 94 which is connected through the connector block 96. Selection for use can be made directly with a switch 98 on the probe unit or alternately a switch pedal unit 100 can be interconnected to control the on-off operation. The output from the tank coil is taken through a blocking capacitor 102.

A feedback circuit, contained within the dotted lines 104 is available for controlling the output of the unit and maintaining it at a desired level. The feedback unit includes a single coil 106 sampling part of the output from the tank coil and a Zener diode 108 which sets a fixed level on the inputs to a Darlington amplifier 110. An intensity control unit 112 is available for adjusting the output level. An adjustment circuit 114 is also provided for initial adjustment of the circuit. By varying the intensity control 112, the output level can be adjusted as desired. The feedback circuit operates to maintain the output at a desired level.

In the aforementioned patent, the output resistor 116 was provided and was connected to ground. Thus, the resistor 116 was available for preventing any high transients from occurring across the output resulting from initial activation of the system. The capacitors 56 and 102 were used as the DC and low frequency blocking capacitors which are interjected between the patient output line and the potentially dangerous internal voltage.

Should the capacitors 56 and 102 become short circuited, the internal B+ voltage, approximately 500 volts, would appear at the output. This voltage would tend to severely damage the patient. To alleviate this condition, the failsafe circuit shown within the dotted lines 118 is provided. This failsafe circuit as shown is the one previously described in connection with FIG. 2.

The high internal voltage appearing at the output, would cause a direct current to flow through the resistor 116 into the gate terminal 34 of the SCR 28. This would cause a low impedance conducting path between the anode and the cathode of the SCR. Since the anode is connected to the B+ of the power supply and the cathode is connected to ground, a short circuit is created across the internal power supply. This would cause the fuse 66 and/or fuse 68 to rupture thereby interrupting power to the entire system.

In the embodiment shown in FIG. 3, the resistor 30 was 75 ohms and the particular SCR which met the required parimeters was either RCA No. S2062M or No. S2600M.

Although the present invention is described in connection with a particular electrosurgical unit, it should be understood that the failsafe system of the present invention could likewise be utilized with other types of circuits. For example, the failsafe system could likewise be utilized with the electrosurgical unit described in my U.S. Pat. No. 4,051,855, also assigned to the assignee of the present invention. Furthermore, it could be utilized with other electrosurgical units, as well as other generators which provide an output voltage which must be monitored.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. In an electrosurge generator energized by a power supply, and producing an output voltage of a desired level, an improvement comprising
    a failsafe circuit for preventing an excessive high output voltage from the electrosurge generator resulting from a failure therein,
    said failsafe circuit including voltage detection means coupled in parallel across the voltage output of the electrosurge generator for detecting an excessive high output voltage of at least a predetermined threshold, and
    a switching circuit means activated by said detection means and connected in parallel across the power supply for short circuiting the power supply without diverting the output current to flow therethrough, thereby removing the power supplied from the power supply to the electrosurge generator.

2. An electrosurge generator as in claim 1, wherein said failsafe circuit comprises a thyristor having a switching junction for providing part of said detection means, and having main terminals connected to the power supply for providing said switching circuit means.

3. An electrosurge generator as in claim 2, wherein said thyristor is an SCR having a gate coupled to the output of the electrosurge generator, and having an anode and a cathode respectively coupled between an output of the power supply and a ground terminal.

4. An electrosurge generator as in claim 3, wherein said power supply is coupled to a source of energy, and further comprising fuse means coupled in series between said power supply and said source of energy, whereby triggering of said SCR causes the power supply to be short circuited and the fuse means to be broken.

5. An electrosurge generator as in claim 3, and further comprising resistor means coupled between the SCR and the power supply to limit a short circuit current in the SCR while permitting an overload limit across the power supply.

6. An electrosurge generator as in claim 3, and further comprising a resistor coupled between the gate and the ground terminal to provide a leakage current path to prevent premature triggering of the SCR.

7. An electrosurge generator as in claim 6, and further comprising capacitor means coupled in parallel to the resistor to thereby filter out any transients to prevent premature triggering of the SCR.

8. An electrosurge generator as in claim 3, wherein said electrosurge generator is an electrosurgical unit having means for selectively providing an unmodulated RF output for a cutting operation and a pulse modulated RF output for a coagulation operation.

9. An electrosurge generator as in claim 8, wherein said electrosurgical unit means comprises an oscillator, an output tank circuit coupled to the oscillator for controlling the frequency of the output signal, a control circuit coupled to the oscillator for selectively producing a modulated and unmodulated output, and a handpiece device coupled to said tank circuit for applying the output voltage to a load.

10. An electrosurge generator as in claim 9, wherein said detection means further comprises a resistor means coupled between said output tank circuit and the gate of said SCR.

* * * * *